US008690792B2

(12) United States Patent  
Horsewood et al.

(10) Patent No.: US 8,690,792 B2
(45) Date of Patent: Apr. 8, 2014

(54) DIRECT ASSAY OF CHOLESTEROL IN SKIN REMOVED BY TAPE STRIPPING

(75) Inventors: Peter Horsewood, Dundas (CA); Robert Zawydiwski, Stoney Creek (CA)

(73) Assignee: Miraculins Inc., Winnipeg (CA)

( * ) Notice: Subject to any disclaimer, the term of this patent is extended or adjusted under 35 U.S.C. 154(b) by 729 days.

(21) Appl. No.: 12/754,134

(22) Filed: Apr. 5, 2010

(65) Prior Publication Data

US 2011/0033879 A1 Feb. 10, 2011

Related U.S. Application Data

(63) Continuation of application No. 11/116,412, filed on Apr. 28, 2005, now abandoned, which is a continuation-in-part of application No. 10/835,397, filed on Apr. 30, 2004, now Pat. No. 7,238,494.

(30) Foreign Application Priority Data

Apr. 28, 2004 (CA) ...................................... 2465427

(51) Int. Cl.
*A61B 10/00* (2006.01)
(52) U.S. Cl.
USPC .............. 600/562; 600/572; 604/290; 435/11
(58) Field of Classification Search
USPC ..................................... 600/562, 572; 435/11
See application file for complete search history.

(56) References Cited

U.S. PATENT DOCUMENTS

| 2,894,511 | A | * | 7/1959 | Devaud | 604/372 |
|---|---|---|---|---|---|
| 3,078,031 | A | * | 2/1963 | Kauffeld | 229/208 |
| 4,055,394 | A | * | 10/1977 | Friedman et al. | 422/401 |
| 4,285,461 | A | * | 8/1981 | Meyers | 229/123.2 |
| 4,458,686 | A | * | 7/1984 | Clark, Jr. | 600/358 |
| 4,532,937 | A | * | 8/1985 | Miller | 600/572 |
| 4,789,629 | A | * | 12/1988 | Baker et al. | 435/7.92 |
| 4,803,048 | A | * | 2/1989 | Nason | 422/401 |
| 5,025,920 | A | * | 6/1991 | Walsh et al. | 206/223 |
| 5,063,026 | A | * | 11/1991 | Wong | 600/572 |
| 5,088,502 | A | * | 2/1992 | Miller | 600/572 |
| 5,100,619 | A | * | 3/1992 | Baker et al. | 422/408 |
| 5,211,286 | A | * | 5/1993 | Turner | 206/223 |
| 5,441,698 | A | * | 8/1995 | Norell | 422/401 |
| 5,489,510 | A | * | 2/1996 | Lopukhin et al. | 435/7.1 |
| 5,876,389 | A | * | 3/1999 | Bouchard et al. | 604/385.16 |
| 5,939,252 | A | * | 8/1999 | Lennon et al. | 435/4 |
| 6,017,767 | A | * | 1/2000 | Chandler | 436/514 |
| 6,033,627 | A | * | 3/2000 | Shields et al. | 422/408 |
| 6,106,732 | A | * | 8/2000 | Johnston et al. | 210/767 |
| 6,365,363 | B1 | * | 4/2002 | Parfenov et al. | 435/11 |
| 6,447,463 | B1 | * | 9/2002 | Borkowski | 600/562 |
| 6,479,073 | B1 | * | 11/2002 | Lucast et al. | 424/448 |
| 6,605,440 | B2 | * | 8/2003 | Maleev et al. | 435/7.1 |
| 6,645,184 | B1 | * | 11/2003 | Zelickson et al. | 604/290 |

(Continued)

*Primary Examiner* — Sean Dougherty (74) *Attorney, Agent, or Firm* — Calfee Halter & Griswold LLP (57) ABSTRACT

Skin cholesterol is measured by applying an adhesive tape onto a selected area of the skin to adhere the tape to the selected skin area and stripping the tape off the selected skin area to obtain a sample representative of the outer stratum corneum layer of the skin, the sample adhering to the tape so as to have exposed skin constituents. The sample is assayed using a detector reagent that specifically binds to cholesterol and in addition has an indicator component that allows quantitation of the amount of cholesterol present in the exposed skin constituents.

16 Claims, 4 Drawing Sheets

(56) References Cited

U.S. PATENT DOCUMENTS

| | | | |
|---|---|---|---|
| 6,689,114 B2 * | 2/2004 | Bouchard et al. | 604/385.14 |
| 6,720,145 B2 * | 4/2004 | Rheins et al. | 435/6.16 |
| 6,875,444 B2 * | 4/2005 | Telesca et al. | 424/443 |
| 7,063,774 B2 * | 6/2006 | Bhullar et al. | 204/403.02 |
| 7,160,256 B2 * | 1/2007 | Perlhagen et al. | 600/580 |
| 7,976,792 B2 * | 7/2011 | Shivji | 422/409 |
| 2002/0197604 A1 * | 12/2002 | Rheins et al. | 435/6 |
| 2003/0045810 A1 * | 3/2003 | Borkowski | 600/562 |
| 2005/0120566 A1 * | 6/2005 | Dworschak et al. | 30/266 |
| 2007/0255177 A1 * | 11/2007 | Pronovost | 600/573 |

* cited by examiner

DIRECT ASSAY OF CHOLESTEROL IN SKIN REMOVED BY TAPE STRIPPING

This application is a continuation-in-part of application Ser. No. 10/835,397, filed Apr. 30, 2004, and the entire contents of which is hereby incorporated by reference.

FIELD OF THE INVENTION

The present invention relates to a method of measuring skin cholesterol. More particularly, the invention pertains to a method for the direct assay of cholesterol in skin samples removed by tape stripping, with a view to identifying individuals at risk of having atherosclerosis as well as those at risk of developing atherosclerosis and similar diseases associated with and attributable to high cholesterol levels.

BACKGROUND OF THE INVENTION

Numerous studies have shown that atherosclerosis and its complications, such as heart attacks and strokes, are major causes of morbidity and mortality in almost all countries of the world.

Cost effective prevention of atherosclerosis requires the identification of individuals at risk, thereby allowing their medical treatment and change of life style. A desired goal is identifying those individuals belonging to the high-risk group but there are difficulties in selecting optimum methods for discriminating individuals at risk.

A widely used method for identifying individuals at risk of having atherosclerosis is based on the measurement of total cholesterol levels in venous blood plasma (Consensus Conference on Lowering Blood Cholesterol to Prevent Heart Disease, JAMA, 1985, 253, pg. 2080). Patients are considered to be at high-risk if their cholesterol level is over 240 mg/dL and there have been recent moves to lower this threshold level to lower values.

However, total cholesterol levels alone do not accurately predict a patient's risk level. A better prediction can be made by analyzing blood plasma lipoproteins; in particular, measurement of low density and high-density lipoprotein (HDL) cholesterol levels is advantageous (Total and High Density Lipoprotein Cholesterol in the Serum and Risk of Mortality, British Medical Journal, 1985, 290, pg. 1239-1243).

Despite their advantage, use of the above methods requires blood sampling after a period of fasting. Additionally, the sampling is uncomfortable, poses a risk of infection and the required analysis of plasma lipoproteins and cholesterol is complicated and expensive. Moreover, studies have shown that blood plasma analysis may not entirely reflect the process of cholesterol accumulation in the arterial wall and other tissues. In many cases, neither plasma cholesterol levels nor even complete lipid profiles correlate with the severity of atherosclerosis.

Significant levels of cholesterol occur in tissue as well as in plasma and it has been shown that tissue cholesterol plays a leading role in development of atherosclerosis. Tissues, including skin, have been identified which accumulate cholesterol in the same way as the arterial wall and studies have demonstrated a close correlation between cholesterol content in the arterial wall and the skin. For example, cholesterol was extracted from lyophilized skin samples and measured using traditional chemical and biochemical techniques. (Nikitin Y. P., Gordienko I. A., Dolgov A. V., Filimonova T. A. "Cholesterol content in the skin and its correlation with lipid quotient in the serum in normals and in patients with ischemic cardiac disease", Cardiology, 1987, II, No. 10, P. 48-51). While useful, this method is too complicated and painful to be employed for large scale population screening.

U.S. Pat. No. 4,458,686 describes a method of quantifying various compounds in the blood directly under the skin or on its surface. The method is based on measuring oxygen concentration changes electrochemically, for instance, via polarography. In the case of non-volatile substances that do not diffuse through the skin, it is necessary to implant enzymes under the skin to effect oxygen changes at the skin surface. This patent also discloses the potential of using such methods to quantify the amount of cholesterol using cholesterol oxidase. The complex instrumentation and procedures needed require the services of highly skilled personnel for making measurements, thus limiting the usefulness of the method for screening large numbers of people.

Determination of the cholesterol content in skin gives a measure of the extent of atherosclerosis and can be obtained through standard laboratory analysis of skin biopsy specimens. However, there is considerable pain involved in taking a skin sample and a risk of infection at the sampling site. In addition, this method has other disadvantages because the thick skin specimens incorporate several skin layers, including the outermost horny layer (stratum corneum), epidermis and dermis. Since the dermal layer is highly vascularized, skin biopsy samples contain blood vessels and blood elements. They may also contain sweat and sebaceous glands and the secretions contained therein. Additionally, subcutaneous fat is located directly under the derma and may also contaminate specimens. Therefore, skin biopsy specimens are heterogeneous and their analysis may give false data on cholesterol content in the skin.

U.S. Pat. No. 5,489,510 describes a non-invasive method for the visual identification of cholesterol on skin using a reagent having a specific cholesterol binding component in combination with a reagent having an indicator component to provide a visual color change corresponding to the presence of the component bound to cholesterol of the skin. The method overcomes many of the objections of earlier procedures and meets many of the desired goals required for a simple mass screening to identify individuals at risk of having atherosclerosis. The procedure is done directly on the palmar skin and, while it is quick and simple, it requires all individuals to be tested to be present at a doctor's office or clinic where the test is conducted. This of course limits effective large scale screening.

Molar ratios of the lipids, including cholesterol, in stratum corneum have been determined on samples obtained by direct, solvent extraction of skin (Norlen L., et al. J. Invest. Dermatology 72-77, 112, 1999). High performance liquid chromatography (HPLC) and gas liquid chromatography in conjunction with mass spectrometry were used to separate and analyze the lipids. The analytical methods are complex, but more importantly, the use of corrosive and irritant organic solvent systems to extract human skin for routine determinations is not practical.

The lipid profile of the stratum corneum layer of skin has been determined using a tape stripping method as described by A. Weerheim and M. Ponec (Arch. Dermatol. Res., 191-199, 293, 2001). In this study, lipids, including cholesterol, were solvent extracted from stratum corneum after tape stripping of skin. The resultant lipid extract was separated by high performance thin-layer chromatography. This method is very laborious. It requires three consecutive solvent systems to effect the separation of the lipids, a staining and charring method to visualize the components and a densitometry step to determine the relative amounts of the lipids. The method does not lend itself to the simple and rapid determination of cholesterol levels in large numbers of samples.

SUMMARY OF THE INVENTION

It is therefore an object of the present invention to overcome the above drawbacks and to provide a simple and non-invasive method of measuring skin cholesterol, which allows for effective large scale screening.

According to a first aspect of the invention, there is provided a method of measuring skin cholesterol, which comprises the steps of:
  a) providing a tape comprising a backing member coated on at least one side thereof with a medical adhesive;
  b) applying the tape onto a selected area of skin to adhere the tape to the selected skin area;
  c) stripping the tape off the selected skin area to obtain a sample representative of an outer stratum corneum layer of the skin, the sample adhering to the tape so as to have exposed skin constituents;
  d) providing a source of an affinity-enzymatic compound of formula A-C-B, wherein A is a detecting agent having affinity for cholesterol, B is an enzymatic visualizing agent and C is a binding agent linking the detecting agent and the visualizing agent to one another;
  e) applying a predetermined amount of the affinity-enzymatic compound onto a predetermined surface area of the sample and allowing the compound to remain in contact therewith for a period of time sufficient to cause binding of the detecting agent to cholesterol present in the exposed skin constituents; and
  f) applying a predetermined amount of a color developing agent onto the predetermined surface area of the sample, whereby the color developing agent reacts with the enzymatic visualizing agent to form a colored product having a color indicative of cholesterol level.

The detecting agent in the aforesaid method is selected from the group consisting of steroid glycosides, triterpene glycosides, hydrophobic proteins, polyene antibiotics and anti-cholesterol antibodies. In one aspect of the invention, the detecting agent is a steroid glycoside, and the steroid glycoside is digitonin.

Further, in the aforesaid method, the enzymatic visualizing agent is an enzyme selected from the group consisting of peroxidase, alkaline phosphatase, urease, galactosidase, glucose oxidase and acetylcholinesterase. In one aspect of the invention, the enzyme is peroxidase, and the peroxidase is horseradish peroxidase.

In a further aspect of the invention, after step (e) the peroxidase is activated with hydrogen peroxide to form an activated peroxidase, and wherein the color developing agent used in step (f) reacts with the activated peroxidase to form the colored product.

In a further aspect of the invention, in step (f) a predetermined amount of an aqueous solution containing hydrogen peroxide and the color developing agent is applied onto the predetermined surface area of the sample.

The color developing agent is selected from the group consisting of 2,2'-azino-di-(3-ethylbenzthiazoline-6-sulfonic acid) and 3,3',5,5'-tetramethyl benzidine. In a particular aspect of the invention, the color developing agent is 3,3'5,5'-tetramethyl benzidine.

The binding agent is a copolymer of maleic anhydride and N-vinylpyrrolidone.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

According to a second aspect of the invention, there is provided a method of measuring skin cholesterol, which comprises the steps of:
  a) providing a tape comprising a backing member coated on at least one side thereof with a medical adhesive;
  b) applying the tape onto a selected area of skin to adhere the tape to the selected skin area;
  c) stripping the tape off the selected skin area to obtain a sample representative of an outer stratum corneum layer of the skin, the sample adhering to the tape so as to have exposed skin constituents;
  d) providing a source of an affinity signal-generating compound of formula A-C-B', wherein A is a detecting agent having affinity for cholesterol, B' is a signal-generating indicator agent and C is binding agent linking the detecting agent and the indicator agent to one another;
  e) applying a predetermined amount of the affinity signal-generating compound onto a predetermined surface area of the sample and allowing the compound to remain in contact therewith for a period of time sufficient to cause binding of the detecting agent to cholesterol present in the exposed skin constituents; and
  f) measuring the signal generated by the indicator agent to provide a value indicative of cholesterol level.

The detecting agent in the aforesaid method is selected from the group consisting of steroid glycosides, triterpene glycosides, hydrophobic proteins, polyene antibiotics and anti-cholesterol antibodies. In one aspect of the invention, the detecting agent is a steroid glycoside, and the steroid glycoside is digitonin.

The indicator agent in the aforesaid method is selected from the group consisting of dyes, fluorophores, radioisotopes, metal sol compounds and chemiluminescent compounds. In one aspect of the invention, the indicator agent is a dye. In another aspect of the invention, the indicator agent is a fluorophore. In a further aspect of the invention, the indicator agent is a radioisotope. In another aspect of the invention, the indicator agent is a metal-sol compound. In a further aspect of this invention the indicator agent is a chemiluminescent compound.

Moreover, in one aspect of the invention, step (f) is carried out by spectrophotometry. In another aspect of the invention, step (f) is carried out by colorimetry. In yet a further aspect of the invention, step (f) is carried out by fluorometry. A further aspect of the invention has step (f) is carried out by means of a radioactivity sensor. In a further aspect of this invention, step (f) is carried out by luminometry.

In the aforesaid method the binding agent is a copolymer of maleic anhydride and N-vinylpyrrolidone.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

According to a third aspect of the invention, there is provided a method of measuring skin cholesterol, which comprises the steps of:

a) providing a tape comprising a backing member coated on at least one side thereof with a medical adhesive;
b) applying the tape onto a selected area of skin to adhere the tape to the selected skin area;
c) stripping the tape off the selected skin area to obtain a sample representative of an outer stratum corneum layer of the skin, the sample adhering to the tape so as to have exposed skin constituents;
d) providing a source of cholesterol oxidase as a detecting agent having affinity for cholesterol;
e) applying a predetermined amount of cholesterol oxidase onto a predetermined surface area of the sample and allowing the cholesterol oxidase to remain in contact therewith for a period of time sufficient to cause oxidation of cholesterol and formation of hydrogen peroxide; and
f) measuring the amount of hydrogen peroxide formed in step (e), the amount of hydrogen peroxide measured being indicative of cholesterol level.

In one aspect of the aforesaid method, step (f) is carried out by means of an electrochemical sensor. In another aspect of the method, step (f) is carried out amperometrically using an electrode. In a further aspect of the method, step (f) is carried out by spectrophotometry after addition of peroxidase and a colorimetric indicator. In one aspect, the peroxidase is horseradish peroxidase. In a further aspect, the colorimetric indicator is 2,2'-azino-di-(3-ethylbenzthiazoline-6-sulfonic acid). In yet a further aspect of the invention, the colorimetric indicator is 3,3',5,5'-tetramethyl benzidine. In a further aspect of the invention, the colorimetric indicator is a multicomponent oxidative coupling reagent of Trinder or Ngo-Lenhoff type.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

The present invention also provides, in a fourth aspect thereof, a kit for use in carrying out a method according to the first aspect. The kit comprises:
the aforesaid tape;
the aforesaid source of affinity-enzymatic compound of formula A-C-B, wherein A, B and C are as defined above; and
a source of the aforesaid color developing agent.

The detecting agent in the aforesaid kit is selected from the group consisting of steroid glycosides, triterpene glycosides, hydrophobic proteins, polyene antibiotics and anti-cholesterol antibodies. In one aspect of the invention, the detecting agent is a steroid glycoside, and the steroid glycoside is digitonin.

Further, in the aforesaid kit, the enzymatic visualizing agent is an enzyme selected from the group consisting of peroxidase, alkaline phosphatase, urease, galactosidase, glucose oxidase and acetylcholinesterase. In one aspect of the invention, the enzyme is peroxidase, and the peroxidase is horseradish peroxidase.

Moreover, the aforesaid kit further includes an aqueous solution containing hydrogen peroxide, the color developing agent being present in said solution. The color developing agent is selected from the group consisting of 2,2'-azino-di-(3-ethylbenzthiazoline-6-sulfonic acid) and 3,3',5,5'-tetramethyl benzidine. In one aspect of the invention, the color developing agent is 3,3'5,5'-tetramethyl benzidine.

Further, in the aforesaid kit, the binding agent is a copolymer of maleic anhydride and N-vinylpyrrolidone.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

The invention further provides, in a fifth aspect thereof, a kit for use in carrying out a method according to the second aspect. The kit comprises:
the aforesaid tape; and
the aforesaid source of affinity signal-generating compound of formula A-C-B', wherein A, B' and C are as defined above.

The detecting agent in the aforesaid kit is selected from the group consisting of steroid glycosides, triterpene glycosides, hydrophobic proteins, polyene antibiotics and anti-cholesterol antibodies. In one aspect of the invention, the detecting agent is a steroid glycoside, and the steroid glycoside is digitonin.

The indicator agent in the aforesaid kit is selected from the group consisting of dyes, fluorophores, radioisotopes, metal sol compounds and chemiluminescent compounds. In one aspect of the inventions, the indicator agent is a dye. In another aspect of the invention, the indicator agent is a fluorophore. In a further aspect of the invention, the indicator agent is a radioisotope. In another aspect of the invention, the indicator agent is a metal-sol compound. In a further aspect of this invention the indicator agent is a chemiluminescent compound.

In the aforesaid kit the binding agent is a copolymer of maleic anhydride and N-vinylpyrrolidone.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

The invention additionally provides, in a sixth aspect thereof, a kit for use in carrying out a method according to the third aspect. The kit comprises:
the aforesaid tape; and
the aforesaid source of cholesterol oxidase.

In the aforesaid kit the peroxidase is horseradish peroxidase. In one aspect of the invention, colorimetric indicator is of 2,2'-azino-di-(3-ethylbenzthiazoline-6-sulfonic acid). In another aspect of the invention, the colorimetric indicator is 3,3'5,5'-tetramethyl benzidine.

Moreover, the backing member of the tape is formed of polyester. The medical adhesive is a pressure-sensitive adhesive. In one aspect of the invention, the medical adhesive is an acrylic based adhesive. In another aspect of the invention, the medical adhesive is a synthetic rubber elastomer adhesive. In yet a further aspect of the invention, the medical adhesive is a silicone based adhesive. In a further aspect, the medical adhesive comprises an elastomer formed of block polymers of styrene-isoprene-styrene or styrene-butadiene-styrene.

Moreover, in all of the aforesaid kits, the tape is carried by a closeable device, the closeable device having a sampling member that carries the tape, and a closure member adapted to engage the sampling member and retain the tape within the device. It is preferable that the tape is sealed within the device when the closure member engages the sampling member. In one aspect, at least the closure member or the sampling member is provided with a peripheral rim, and the other of the closure member or the sampling member is provided with a peripheral groove adapted to receive the rim so that the tape is sealed within the device. The closure member can be connected to the sampling member by a hinge.

In one aspect of the invention, at least a portion of the sampling member is adapted to be cut from the closeable device to form a dipstick, the dipstick having a first end thereof devoid of tape, and a second end thereof with the tape.

In a second aspect of the invention, at least a portion of the sampling member is adapted to be cut from the closeable device to form a disk, the disk having the tape provided on one face thereof.

Further, the aforesaid kits can further comprise a cutting tool adapted to cut the disk from the device. To show where the cutting tool is to be applied the the closeable device can be provided with a marker on an outside surface thereof.

Moreover, the cutting tool can be provided with a plunger to eject the disk from the end of the cutter after the disk is cut.

The invention also provides for a tape stripping device for use in obtaining skin samples, the device comprising:
a) a sampling member having a surface,
b) a tape provided on at least a portion of the surface of the sampling member, the tape having a medical adhesive presented away from the surface; and
c) a closure member adapted to engage the sampling member and retain the tape within the device.

It is preferable that the tape is sealed within the device when the closure member engages the sampling member. In one aspect, at least the closure member or the sampling member is provided with a peripheral rim, and the other of the closure member or the sampling member is provided with a peripheral groove adapted to receive the rim so that the tape is sealed within the device. The closure member can be connected to the sampling member by a hinge.

In one aspect of the invention, at least a portion of the sampling member is adapted to be cut from the closeable device to form a dipstick, the dipstick having a first end thereof devoid of tape, and a second end thereof with the tape.

In a second aspect of the invention, at least a portion of the sampling member is adapted to be cut from the closeable device to form a disk, the disk having the tape provided on one face thereof.

Applicant has found quite surprisingly that the measurement of skin cholesterol can be carried out directly on the skin sample adhering to the aforementioned tape. The procurement of skin samples removed by tape stripping from donor individuals allows assays to be conducted at distant and centralized sites and also allows assays from many individuals to be run concurrently. Thus, the method according to the invention is suitable for large scale screening of individuals for assessing their risk of cardiovascular disease.

BRIEF DESCRIPTION OF THE DRAWINGS

For a better understanding of the present invention and to show more clearly how it would be carried into effect, reference will now be made by way of example, to the accompanying drawings that show a preferred embodiment of the present invention, and in which.

DETAILED DESCRIPTION OF THE INVENTION

Use is preferably made of a tape comprising a backing member formed of polyester. The tape is coated on at least one side thereof with a medical adhesive. The term "medical adhesive" as used herein refers to an adhesive which is hypoallergic and safe for application to the skin. Such an adhesive is preferably a pressure-sensitive adhesive, for example, an adhesive comprising an elastomer formed of block polymers of styrene-isoprene-styrene or styrene-butadiene-styrene.

As can be appreciated, there are many classifications and types of adhesives. In general, any adhesive suitable for use with this invention is a medical adhesive as defined above to ensure there will be generally no problems with allergic reactions when the adhesive was applied to the skin for sampling. The inventors tested several types of adhesives for use in taking a skin sample; the majority of these were pressure sensitive acrylic based adhesives, but several synthetic rubber type elastomer adhesives and silicone based adhesives were also tested.

The inventors have found that synthetic rubber adhesives based on block copolymers of styrene and butadiene or styrene and isoprene perform well for this invention. An example of a synthetic rubber adhesive is a synthetic Kraton™ type adhesive (latex free) based on a block copolymer of styrene and butadiene. Such an adhesive provided better stability for skin samples to facilitate transportation of the samples for subsequent analysis.

A further preferred adhesive tape for use in the method of the invention is a double-coated pressure-sensitive medical grade tape. Examples of such a medical grade tape are those sold by 3M under Product #9877, or by Adhesive Research, Inc. under Product #8570.

A list of some of the other tapes that have been tested by the inventors is shown in the accompanying table. The one requirement that is constant is the use of a medical grade tape that is hypoallergenic.

TABLE 1

| Adhesive | Tape Product Name | Supplier |
| --- | --- | --- |
| MA 27 Acrylic | AR 8570 | Adhesive Research, Inc. |
| MA 38 Acrylic | AR 7396 | Adhesive Research, Inc. |
| HY-3 Acrylic Urethane liner | AR 8311 | Adhesive Research, Inc. |
| MA 65 Acrylic | AR 8944 | Adhesive Research, Inc. |
| MA 61 Acrylic | AR 8890 | Adhesive Research, Inc. |
| Acrylic | AR 8968 | Adhesive Research, Inc. |

TABLE 1-continued

| Adhesive | Tape Product Name | Supplier |
|---|---|---|
| AS 124M Acrylic | AR 8651 | Adhesive Research, Inc. |
| Acrylic | MA 38 | Adhesive Research, Inc. |
| MA 31 Acrylic | MA 31 | Adhesive Research, Inc. |
| MA24 rosin tackified polyisubutylene | MA 24A | Adhesive Research, Inc. |
| Rubber solution | MA 70 | Adhesive Research, Inc. |
| Acrylic | MA 46 | Adhesive Research, Inc. |
| Acrylic acid free | #888 | 3M |
| Silicone Duragesic base | N/A | Alza Corporation |
| Silicone/acrylic | 702 | Scapa Group PLC |
| Silicone/silicone | 705 | Scapa Group PLC |

It can be appreciated that the adhesive tapes listed in Table 1 is not meant to be exhaustive, but merely illustrative of different adhesive tapes that are suitable for use with this invention at the present time, and that other adhesive tapes that will be apparent to those skilled in the art are contemplated by this invention.

Double-coated pressure-sensitive tapes are generally available with an easily removable protective liner. The liner protects the tape from adhering until it is removed and keeps the adhesive from becoming contaminated. Liners may be placed on either side of the double-coated tape or the tape may have a single liner and be wound onto itself, thereby protecting both surfaces.

Liners with differential release properties may be used so that a first side of adhesive may be exposed while protecting the second adhesive surface. A double-coated tape with differential liners is particularly advantageous for skin sampling. Removal of the first liner allows the tape to be stuck onto the backing support of a sampling device and leaves the skin-sampling side covered with the second liner. This second liner protects the skin sampling adhesive area from sticking and from contamination until it is to be used. When required for skin sampling, the second liner is removed.

The tape can be applied onto any part of skin, but the most suitable part is the surface of a palm because the palm does not have sebaceous glands whose secretions contain cholesterol which may affect results. Additionally, the skin on the palm is readily accessible for sampling.

It is desirable to obtain uniform amounts of skin samples for analysis. Application of the adhesive tape for sampling is typically and routinely done using a single application of the tape to the skin. Additional amounts of stratum corneum material can be obtained by additional applications of the tape to the skin. Each subsequent application of the tape to the skin results in additional skin adhering to the tape. This process continues until the tape becomes saturated with skin material after which it is no longer sticky. The number of applications required to saturate a tape depends on the type of adhesive used, but for the most commonly used adhesive tapes, saturation is achieved with less than ten applications, for example, but not limited to, three to seven applications. Applying tape to a fresh area of skin for each subsequent stripping results in better and faster saturation of the tape. Therefore, for consistent and good sampling, it is convenient to make ten applications of a tape to the skin, using new areas of skin for each application.

The total amount of cholesterol present in the skin sample on the adhesive tape is related to the size of the skin sample obtained. Moreover, a consistent skin sample size is required in order to compare relative levels of skin cholesterol between different individuals.

Obtaining consistently sized skin samples from various individuals (or repeated samples from the same individual) is accomplished by the following steps. First, as previously described, the skin sample is taken by applying the adhesive tape repeatedly to the skin such that it becomes saturated with skin and is no longer sticky. The tape becomes saturated with skin after about three to seven applications and ten applications are routinely done to ensure saturation. Next, to obtain a constant area of skin sample to be assayed, a fixed sized area (for example, as will be hereinafter become apparent from Examples 2 and 3) from the skin-sampling device is removed, and immersed in standardized volumes of detector and indicator reagents, as will also be described hereinafter.

After skin sampling, the sampling device is closed and shipped to a central laboratory for assay of cholesterol.

When using a compound of formula A-C-B or A-C-B' for the analysis of cholesterol in the skin samples, the detecting agent A can be for example a steroid glycoside, a triterpene glycoside, a hydrophobic protein, a polyene antibiotic or an anti-cholesterol antibody. Use is preferably made of a steroid glycoside, such as digitonin. The binding agent C, on the other hand, is preferably a copolymer of maleic anhydride and N-vinylpyrrolidone.

In the case where use is made of a compound of formula A-C-B, the enzymatic visualizing agent B is preferably an enzyme selected from the group consisting of peroxidase, alkaline phosphatase, urease, galactosidase, glucose oxidase and acetylcholinesterase. Peroxidase such as horseradish peroxidase is preferred. In this particular case, after step (e), the peroxidase is activated with hydrogen peroxide to form an activated peroxidase, and the color developing agent used in step (f) reacts with the activated peroxidase to form the aforesaid colored product. To this end, a predetermined amount of an aqueous solution containing hydrogen peroxide and the color developing agent is applied in step (f) onto the predetermined surface area of the sample. Examples of suitable color developing agents which can be used in step (f) include 2,2'-azino-di-(3-ethylbenzthiazoline-6-sulfonic acid) and 3,3',5,5'-tetramethyl benzidine. 3,3'5,5'-Tetramethyl benzidine is preferred.

In the case where use is made of a compound of formula A-C-B', the indicator agent B' can be for example a dye, a fluorophore, a radioisotope, a metal sol compound or a chemiluminescent compound. When the indicator agent is a dye, step (f) can be carried out by spectrophotometry, such as colorimetry. When the indicator agent is a fluorophore, step (f) can be carried out by fluorometry. When the indicator agent is a radioisotope, step (f) can be carried out by means of a radioactivity sensor. When the indicator agent is a metal-sol compound, step (f) can be carried out by colorimetry. When the indicator agent is a chemiluminescent compound, step (f) can be carried out by luminometry.

In the case where use is made of cholesterol oxidase as a detecting agent having affinity for cholesterol, step (f) is preferably carried out by means of an electrochemical sensor, for instance, amperometrically using an electrode. Step (f) can also be carried out by spectrophotometry after addition of peroxidase and a colorimetric indicator. The peroxidase used is preferably horseradish peroxidase. Examples of suitable colorimetric indicators which can be used include 2,2'-azino-di-(3-ethylbenzthiazoline-6-sulfonic acid) and 3,3',5,5'-tetramethyl benzidine. A colorimetric indicator consisting of a multicomponent oxidative coupling reagent of Trinder or Ngo-Lenhoff type can also be used. When use is made of peroxidase and a colorimetric indicator, the aforementioned kit for carrying out the method according to the third aspect of the invention further comprises a source of peroxidase and a source of the colorimetric indicator.

The method, according to the invention, achieves a simple, high-throughput skin cholesterol assay.

Example 1

A double-coated pressure-sensitive medical grade tape having a protective release liner on an upper sampling side and sold by Adhesive Research, Inc. was used. A piece of tape 1 inch by 1 inch was cut. The piece of tape was stuck, using the exposed, lower adhesive surface to one end of a 1 inch by 3 inch thin plastic (white polystyrene) member, leaving a 1 inch by 2 inch piece of uncovered plastic as a handle for applying the tape to the skin and for labeling the sample.

To obtain a skin sample, the protective liner was removed and the exposed adhesive area applied to a clean dry section of skin. Pressure was applied to the back of the plastic member over the adhesive area to effect good contact of the adhesive with the skin. The plastic member with the attached tape and stratum corneum sample was then peeled from the skin.

The sample was cut into four equal pieces each measuring ½ inch by ½ inch. One piece was placed in a well of a 12-well tissue culture plate, or similar container, with the skin sampling side facing up. An aliquot of reagent of the type A-C-B was then applied onto a predetermined surface area of the skin sample. The A-C-B reagent used was a conjugate of digitonin (A) linked to horseradish peroxidase (B) through a maleic anhydride-N-vinylpyrrolidone copolymer (C). The reagent was left in contact with the skin sample for fifteen minutes at room temperature, after which it is removed by aspiration. Thereafter, the sample was washed with three separate aliquots of a wash solution to remove non-specifically bound reagent. The piece was then placed in a new, clean well of a 12-well tissue culture plate, or similar container, with the skin sampling side facing up. An aliquot of substrate solution was applied to the sample and left in contact with the skin sample for about fifteen minutes at room temperature. The substrate solution used was Enhanced K-Blue reagent available from Neogen Corp. (Lexington, Ky., USA) and containing hydrogen peroxide and tetramethyl benzidine as color developing agent. An aliquot of the developed substrate solution was removed from the well and added to an aliquot of 1 N sulfuric acid in a well of a 96-well microwell plate. The optical density of the resulting solution, which is a measure of the amount of cholesterol in the skin sample, was read at about 450 nm on a plate reading spectrophotometer.

Example 2

Figure 1:
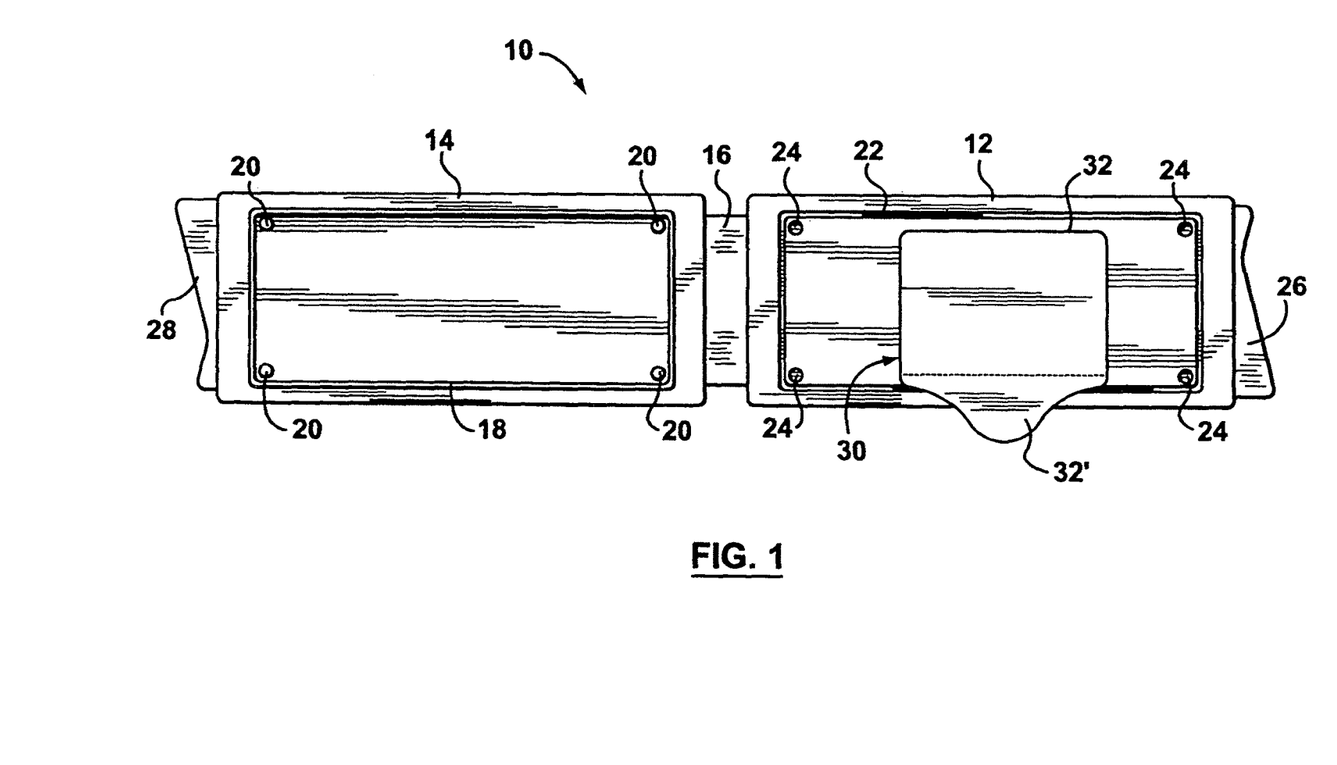
FIG. 1 is a top view of a sampling device as used in Example 2.

Use was made of a sampling device as shown in FIG. 1. The sampling device, which is generally designated by reference numeral 10, is formed of plastic (polypropylene) and comprises a sampling member 12 connected to a closure member 14 by an integral hinge 16. The closure member 14 has a peripheral rim 18 and four pins 20, adapted to lock into, respectively, a peripheral groove 22 and four holes 24 formed in the sampling member 12. Folding the hinge 16 causes engagement of the rim 18 with the groove 22 and of the pins 20 with the holes 24, thereby ensuring that the two halves of the device 10 remain closed and sealed to prevent dust and contamination of the interior surfaces. The outer surface (not shown in FIGS. 1 and 2) of the closure member 14 has a flat area for receiving a label and barcode strip, for sample identification. The sampling member 12 and closure member 14 are respectively provided with finger-tabs 26 and 28 for opening the device 10.

Figure 2:
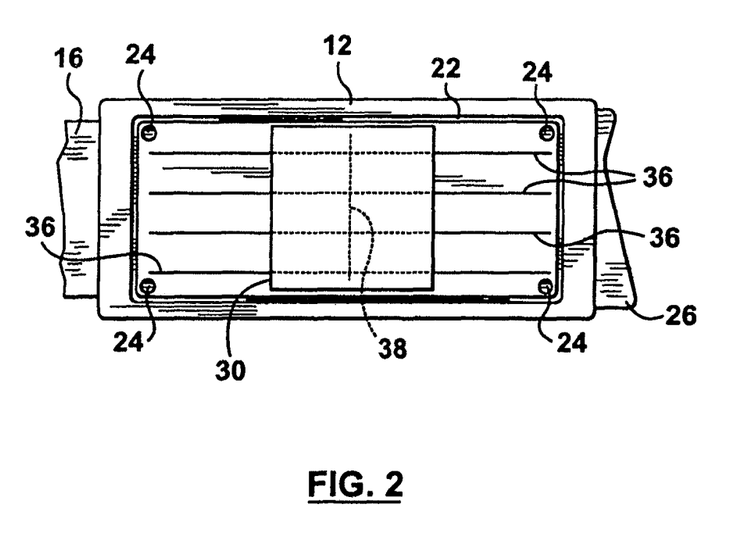
FIG. 2 is a fragmentary view of the sampling device illustrated in FIG. 1, showing details of the sampling member thereof.

A double-coated pressure-sensitive medical grade tape 30 having a protective Kraft paper release liner 32 and sold by 3M under Product #9877 was adhered to the central area of the sampling member 12. The release liner 32 is wider than the adhesive tape 30, thereby defining a strip 32' along one edge with no attached tape. This strip 32' of liner overhangs the edge of the device to form a tab for easy removal of the liner. Immediately before use, the liner 32 is removed using the overhanging tab 32' and this exposes the adhesive of the tape 30 for skin sampling.

The palmar skin area for sampling was cleaned and dried. The tape 30 with the exposed adhesive was applied onto the palm. The tape 30 was pressed against the skin by applying pressure to the back of the sampling member 12 above the adhesive area, thereby causing adherence of the stratum corneum layer. The device 10 was peeled away, reapplied to a new area of the palm and again pressed to the skin. The device is peeled away and applied to the palmar skin in this way for a total of 10 applications.

At least two small dipsticks 40 (see FIG. 3) about four mm in width were cut from the device 10 after application to the skin as follows. Referring to FIG. 2, an end portion of the sampling member 12 was removed by cutting along the portion of groove 22, which is adjacent to the tab 26. Three cuts were then made along guide lines 36 (shown in FIG. 2) molded into the sampling member 12, to delineate the four mm sticks, cutting from the edge to just past the centre line. The two 4 mm wide sticks were released from the sampling member 12 by making a third cut across the center of the member 12, using guide line 38 molded into the member 12. Sticks 40 had a first end portion 42 devoid of tape and a second end portion 44 with tape having the skin sample adhered thereto.

Figure 3:
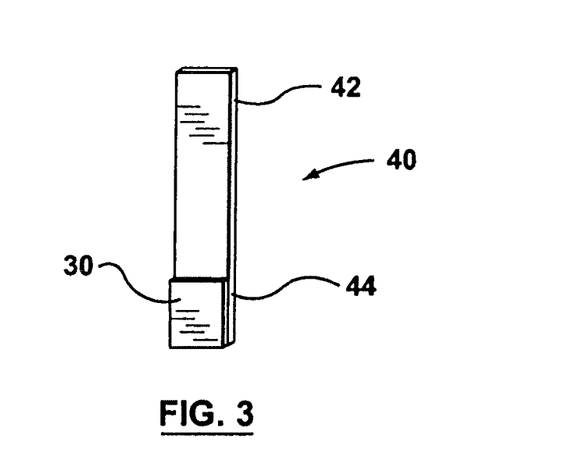
FIG. 3 is a perspective view of a dipstick cut from the sampling device of this invention.

The sticks were each placed into approximately 100 µA solution of an A-C-B reagent in wells of a 96-well microwell plate (not illustrated). The reagent was a conjugate of digitonin (A) linked to horseradish peroxidase (B) through a maleic anhydride-N-vinylpyrrolidone copolymer (C) and was used at a concentration of approximately 1 µg/mL. The sticks were left in the solution for about fifteen minutes at room temperature, after which they were removed and placed into new wells of a microwell plate containing approximately 200 µL of wash solution. The microwell plate was agitated to effect washing and after about one minute the sticks were removed to new wells containing approximately 200 µL of fresh wash solution and again agitated for about one minute. Washing with agitation was done a third time, after which the sticks were removed and placed in approximately 100 µL of a substrate solution (Enhanced K-Blue reagent). The sticks were then incubated with the substrate solution, in the dark, for about fifteen minutes at room temperature. The microwell plate can be shaken during this step.

After the sticks were incubated, the sticks can then be removed. Approximately one hundred (100) µL of 1 N sulfuric acid is then added to the wells with the substrate solution to stop further reaction, and the optical density of the resulting solution was read at about 450 nm on a plate reading spectrophotometer, to provide a measure of the amount of cholesterol in the skin sample.

Example 3

To allow many samples from Example 2 to be processed together requires that the dipsticks 40 be held in a configuration that matches that of a standard 96-well (8×12) microplate. Instruments are available that can dispense reagents into these plates and also to wash the wells, a requirement that is necessary to prevent reagent carry-over between assay steps. Spectrophotometers that can read the coloured solutions directly in the wells at the final step of the assay are also readily available. However, for such an application, the protruding part of the dipsticks from the wells, and the fixtures that hold them, prevent easy access to the wells for dispensing and washing steps. This results in a dipstick assay that requires customized equipment and/or more manual steps than conventional assays run in microwells.

Figure 4:
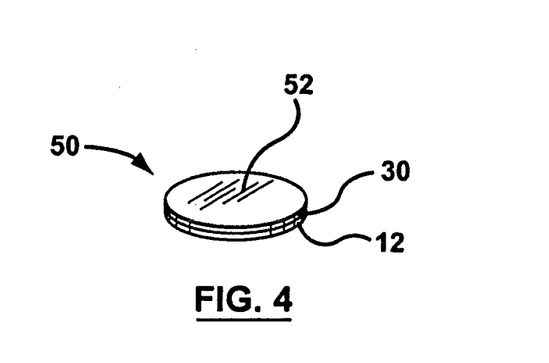
FIG. 4 is a perspective view of a disk cut from the sampling device of this invention in an alternative embodiment.
Figure 5:
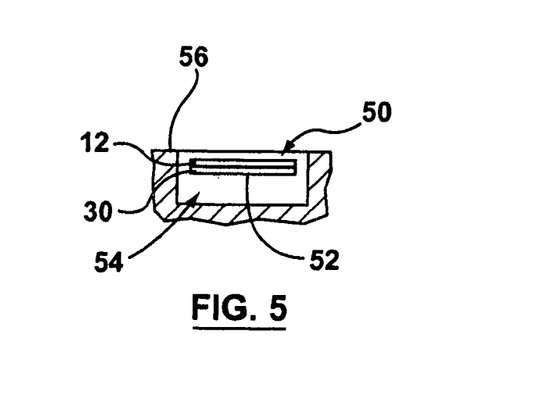
FIG. 5 is a cross-sectional view of a disk from FIG. 4 in the well of a microwell plate.

Batch processing of many samples can be achieved by removing small disks 50 (see FIG. 4) having skin samples 70 adhered to the adhesive tape 30 from the sampling device on one face 52 thereof (skin sample 70 and adhesive 30 are generally illustrated in the Figures as adhesive 30 for purposes of clarity, however, it is to be understood that the adhesive 30 will have skin 70 thereon after application of the device to, for example, the palm of a person), and then processing these disks in the wells 54 of a microplate 56, as shown in FIG. 5. In this manner there are no protrusions above the well and so readily available automated liquid dispensing and washing equipment can be used to add reagents required for cholesterol assay. The disks are sized to fit into the wells of a microplate, yet remain free and not become wedged or trapped within the well. For example, but not limited to, disks that are smaller than 6.0 mm diameter will fit into the wells of all commonly manufactured microplates. It can be appreciated, however, that disks that are too small will have insufficient amount of skin that will compromise assay sensitivity and reproducibility. It has been found that disks 5 to 6 mm in diameter are best suited for assay in 96-well microplates. However, it can be appreciated that the invention is not limited to these dimensions, and that other disk sizes are contemplated for different wells and microplates, as would be apparent to those skilled in the art.

In addition, when the disks are placed in the well, they should not float with the skin-side up since this will contact the dispensing and aspiration tubes that are inserted in the wash steps. Therefore, if the sampling device is constructed of materials that are less dense than water the disks should be added to the well with the skin side down. If the sampling device is constructed of materials that are more dense than water, then the disk is best added with the skin side up and the height of the dispensing and aspiration tubes adjusted so that they do not touch the skin surface.

Either a customized cutting tool or a single-hole paper punch sized 3/16 in. (4.76 mm) can be used to remove disks from the sampling device. The disks must be cut from the device such that any anvil-type part used to eject the disk from a punch or cutting tool must not contact the skin. Thus, when using a paper punch the anvil should contact the back of the device (non-skin side) when cutting and ejecting a disk.

Figure 6:
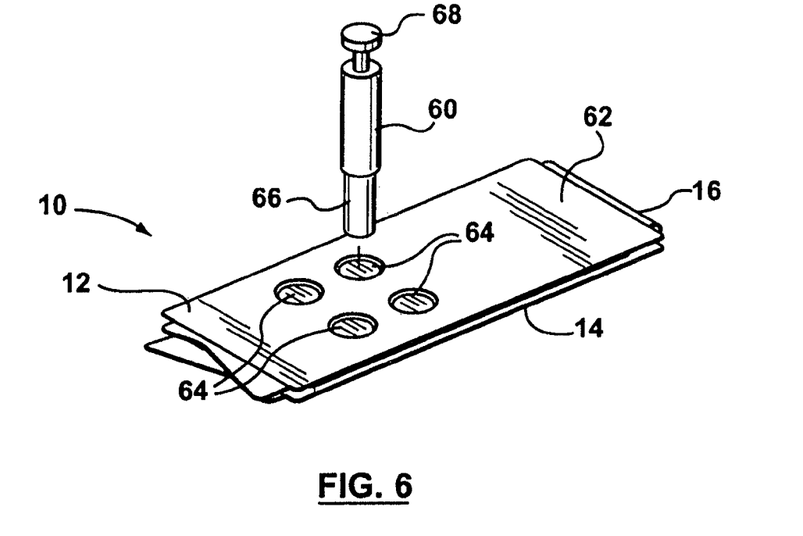
FIG. 6 is a perspective view of the sampling device with cutting tool to produce a disk of FIG. 4.
Figure 7:
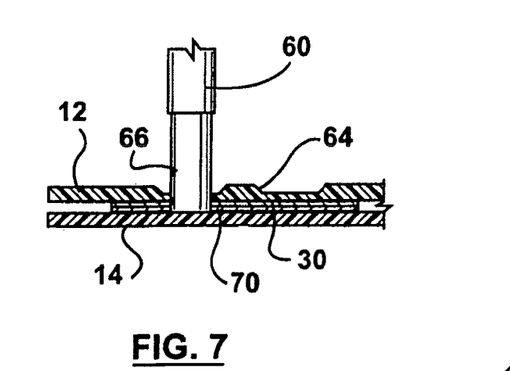
FIG. 7 is a cross-sectional view of the sampling device with cutting tool to produce a disk of FIG. 4.

Referring to FIGS. 6 and 7, a cutting tool 60 removes a disk from the device 10 of FIG. 1 when the device 10 is in a folded over (closed) position, as illustrated. The closed device is placed on a firm surface (not illustrated) with the outer surface 62 of the sampling member 12 of the device facing up. The cutting tool 60 is inserted in a circular depression 64 that can be provided on the outer surface 62 of the sampling member 12 of device 10 and the cutting tool 60 is then pressed down to cut through the plastic and the tape 30/skin 70 sample. The cutting tool 60 is not pressed down so far, however, so as to cut through the plastic of the closure member 14 of the device 10.

Figure 8:
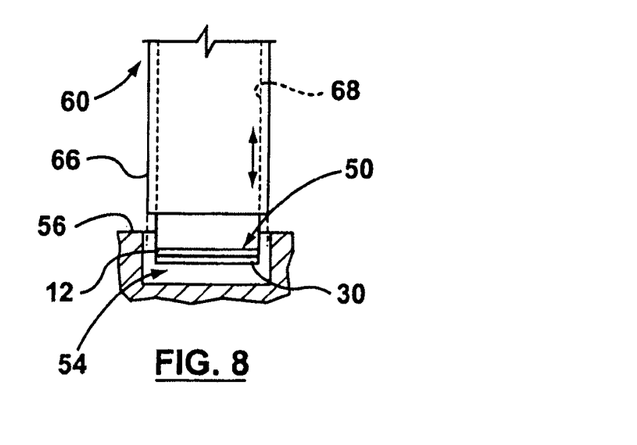
FIG. 8 is a cross-sectional view showing the cutting tool placing the disk in the well of a microwell plate.

Once a required disk 50 has been cut from the device 10, the end 66 of the cutting tool 60 with the disk 50 is placed into a designated well 54 of the microwell plate 56 (see FIG. 8) and plunger 68 of the cutting tool 60 is depressed to eject the disk with the skin sample on the adhesive tape into the well 54.

When all the designated wells of the microwell plate are provided with a disk, the microwell plate is placed on automated plate reader/washer and approximately 100 µL of detector reagent is added to all the wells and the disks are incubated for approximately fifteen minutes at generally room temperature (20-24° C.). The reagent can be a solution of an A-C-B reagent as defined in Example 2.

The detector reagent is then aspirated and approximately 250 µL of wash buffer is added to the wells. The plate can be shaken for approximately thirty seconds after the addition of the wash buffer, removing excess detector reagent, and then left for approximately a further ninety seconds. The wash step can be repeated two or more times as necessary. It is found that three wash steps are satisfactory.

After the wells are washed, approximately 100 µL of Enhanced K-Blue substrate is added to the wells and allowed to incubate with the washed disk for approximately fifteen minutes at generally ambient room temperature (as previously described). The microwell plate can be shaken during this step, and, as in Example 2, the incubation can be in the dark.

The reaction is then stopped by the addition of approximately 100 µL of 1 N sulphuric acid to the wells, and the plate is shaken to mix the solutions. Approximately 100 µL of the stopped substrate is then removed and transferred to the wells of a new plate and read at about 450 nm on a plate reading spectrophotometer and analyzed as previously described to determine the relative level of skin cholesterol for each donor.

In the above examples, it can be appreciated the invention is not intended to be limited to the exact values specified in the Examples and that variations from the volumes, times, temperatures, and wavelengths stated can be made by those skilled in the art without affecting the scope of the invention, hence the use of the terms "approximately" and "about."

The preceding description is meant to be illustrative only and not limiting. Other embodiments of this invention will be apparent to those of ordinary skill in the art in view of this description.

While the embodiments of the invention disclosed are presently considered to be preferred, various changes and modifications can be made without departing from the scope of the invention. The disclosure is intended to be illustrative and not exhaustive. This description will suggest many variations and alternatives to one of ordinary skill in this art. All these alternatives and variations are intended to be included within the scope of the claims. Those familiar with the art may recognize other equivalents to the specific embodiments described that are also intended to be encompassed by the claims.

We claim:

1. A tape stripping device for use in obtaining skin samples, the device comprising: a) a sampling member including an interior surface and an outer surface, either the interior surface or the outer surface including releasable sections of the sampling member; b) the releasable sections delineated by indentations in the sampling member; c) a tape provided on the interior surface of the sampling member, the tape covering at least a portion of a plurality of the releasable sections, the tape having a medical skin stripping adhesive presented away from the interior surface; and d) a closure member adapted to engage the sampling member and seal the tape within the device.

2. A device as claimed in claim 1, wherein the tape is sealed within the device when the closure member engages the sampling member.

3. A device as claimed in claim 2, wherein at least the closure member or the sampling member is provided with a raised peripheral rim.

4. The device as claimed in claim 3 wherein the other of the closure member or the sampling member is provided with a peripheral groove adapted to receive the raised peripheral rim so that the tape is sealed within the device when the device is closed.

5. The device as claimed in claim 3 wherein the raised peripheral rim is configured to provide a void between the closure member and the tape when the device is closed.

6. The device as claimed in claim 3 wherein the raised peripheral rim is configured to provide a sealed void between the closure member and the tape when the device is closed.

7. A device as claimed in claim 1, wherein the closure member is connected to the sampling member by a hinge.

8. A device as claimed in claim 7, wherein the sampling member, the closure member and the hinge are integrally formed.

9. A device as claimed in claim 8, wherein the sampling member, the closure member and the hinge are formed from plastic.

10. A device as claimed in claim 1, wherein the closure member comprises an outer surface including a flat area for receiving a label or a barcode strip.

11. A device as claimed in claim 1, wherein at least one of the sampling member and the closure member is provided with a finger-tab for opening the device.

12. A device as claimed in claim 1, wherein the sampling member and the closure member are each provided with finger-tabs for opening the device.

13. A device as claimed in claim 1, further comprising a release liner adhered to the tape, the release liner including an overhanging tab extending beyond an edge of the sampling member.

14. A device as claimed in claim 1, wherein the indentations of the sampling member comprises a plurality of guidelines disposed on the interior surface of the sampling member, the guidelines delineating the releasable sections, and wherein the releasable sections are adapted to be cut along the guidelines to form at least one dipstick, the at least one dipstick having a first end thereof devoid of tape, and a second end thereof with tape.

15. A device as claimed in claim 1, wherein the indentations of the sampling member comprises at least one circular depression disposed on the outer surface of the sampling member, the at least one circular depression delineating at least one of the releasable sections, and wherein the at least one of the releasable sections is adapted to be cut through the circular depression to form at least one disk, the at least one disk having the tape provided on one face thereof.

16. In combination, a device as claimed in claim 15 and a cutting tool, the cutting tool adapted to cut the at least one disk through the outer surface of the sampling member, the cutting tool comprising a plunger for ejecting the disk.

* * * * *